United States Patent [19]
Gaffney et al.

[11] Patent Number: 5,703,254
[45] Date of Patent: Dec. 30, 1997

[54] PROPYLENE OXIDE PROCESS USING MIXED PRECIOUS METAL CATALYST SUPPORTED ON ALKALINE EARTH METAL CARBONATE

[75] Inventors: Anne M. Gaffney, West Chester; Andrew P. Kahn, Eagleville; Rangasamy Pitchai, West Chester, all of Pa.

[73] Assignee: Arco Chemical Technology, L.P., Greenville, Del.

[21] Appl. No.: 724,936

[22] Filed: Oct. 2, 1996

[51] Int. Cl.$^6$ ............................................. C07D 301/03
[52] U.S. Cl. ............................................. 549/536
[58] Field of Search ............................. 502/347, 340, 502/174; 549/536, 537

[56] References Cited

U.S. PATENT DOCUMENTS

| | | | |
|---|---|---|---|
| 2,040,782 | 5/1936 | van Peski | 260/54 |
| 2,143,371 | 1/1939 | Francon | 260/348 |
| 2,615,900 | 10/1952 | Sears | 260/348.5 |
| 3,773,693 | 11/1973 | Calcagno et al. | 252/466 |
| 3,844,981 | 10/1974 | Cusumano | 252/471 |
| 3,956,191 | 5/1976 | Cusumano | 252/474 |
| 4,007,135 | 2/1977 | Hayden et al. | 252/467 |
| 4,361,504 | 11/1982 | Solomon et al. | 252/463 |
| 4,366,092 | 12/1982 | Winterton | 252/471 |
| 5,112,795 | 5/1992 | Minahan et al. | 502/324 |

FOREIGN PATENT DOCUMENTS

| | | |
|---|---|---|
| 1282772 | 4/1991 | Canada. |
| 0480537 | 4/1992 | European Pat. Off.. |

OTHER PUBLICATIONS

Hayes, "The Role of Reaction Products In The Silver-Catalyzed Oxidation of Ethylene", *Can. J. Chem.* 38, 2256–2268 (1960).

Flank et al., "The Geometric Factor in Ethylene Oxidation Orer Gold–Silver Alloy Catalysts", *J. Catalysis*, 8, 316–325 (1967).

Geenen et al., "A Study of the Vapor–Phase Epoxidation of Propylene and Ethylene on Silver and Silver–Gold Alloy Catalysts", *J. Catalysis* 77, 499–510 (1982).

*Primary Examiner*—Alan L. Rotman
*Assistant Examiner*—Garth M. Dahlen
*Attorney, Agent, or Firm*—Stephen D. Harper

[57] ABSTRACT

Propylene is oxidized to propylene oxide in the vapor phase using oxygen and a supported catalyst comprising silver, gold, a potassium promoter such as potassium nitrate or potassium carbonate and a support comprised in whole or in substantial part of an alkaline earth metal carbonate.

20 Claims, No Drawings

5,703,254

PROPYLENE OXIDE PROCESS USING MIXED PRECIOUS METAL CATALYST SUPPORTED ON ALKALINE EARTH METAL CARBONATE

FIELD OF INVENTION

This invention relates to a process for the direct oxidation of propylene to propylene oxide in the vapor phase using molecular oxygen. In particular, the invention pertains to the use of a catalyst comprised of silver, gold and a potassium promoter supported on an alkaline earth metal-containing carbonate.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier such as alpha alumina upon which the silver and promoters are deposited. A review of the direct oxidation of ethylene in the presence of supported silver catalysts is provided by Sachtler et al. in *Catalysis Reviews: Science and Engineering*, 23 (1&2), 127–149 (1981).

It is also well-known, however, that the catalysts and reaction conditions which are best suited for ethylene oxide production do not give comparable results in the direct oxidation of higher olefins such as propylene. The discovery of processes capable of providing propylene oxide by vapor phase direct oxidation in higher yields than are presently attainable thus would be most desirable.

The incorporation of gold into a supported silver catalyst has occasionally been suggested in order to modify the catalytic performance of such materials in ethylene oxidation reactions. See, for example, U.S. Pat. Nos. 4,366,092 (Winterton), 3,773,693 (Calcagno et al.), 5,112,795 (Minaban et al.), 2,040,782 (van Peskl), 3,844,981 (Cusumano), 4,361,504 (Solomon et al.), and 4,007,135 (Hayden et al.). However, there has been no appreciation that gold could significantly improve the ability of certain supported silver catalysts to selectively convert propylene to propylene oxide using molecular oxygen. In fact, a study of propylene oxidation on Ag—Au alloy catalysts published by Geenen et al. [*J. Catalysis* 77, 499–510 (1982)] concluded that selectivity to acrolein increases, and selectivity to propylene oxide decreases, with increasing gold content.

We have now unexpectedly discovered that a catalyst which is highly selective for the direct production of propylene oxide from propylene is obtained by using an alkaline earth metal carbonate as a support in combination with silver, gold and a potassium promoter. Also surprising was the finding that such catalysts are capable of selective propylene oxidation in the absence of the gaseous chloride and nitric oxide promoters which have heretofore been commonly used to improve epoxide selectivity in vapor phase processes of this type.

SUMMARY OF THE INVENTION

This invention provides a process for producing propylene oxide wherein a feed stream comprised of oxygen and propylene is contacted in the vapor phase at a temperature of 180° C. to 350° C. with a supported catalyst comprising (a) a support comprised of an alkaline earth carbonate;
(b) a catalytically effective amount of silver;
(c) an amount of gold effective to improve selectivity to propylene oxide; and
(d) a promoting amount of a potassium promoter derived from a potassium salt comprising a potassium cation and an oxyanion selected from the group consisting of nitrogen oxyanions, carbon oxyanions and precursors thereof.

DETAILED DESCRIPTION OF THE INVENTION

The present invention is directed to a process for the vapor phase oxidation of propylene oxide, i.e., an epoxidation process performed in the presence of an oxygen-containing gas and a particular class of supported silver catalysts.

The support material used in the present invention is selected from one of several carbonate-containing carrier materials. The carbonate employed is an inorganic carbonate having a cation which is an alkaline earth metal ion, particularly calcium, strontium, magnesium or barium with calcium being most preferred. Such carbonates are capable of providing exceptionally high propylene oxide selectivities and have been found to be surprisingly superior to other support materials in this respect. Suitable carbonate supports are described, for example, in Canadian Patent No. 1,282,772. The carrier is one in which the carbonate is the predominate (i.e., at least 50% by weight) or, preferably, substantially the exclusive component of the support (i.e., the support consists essentially of one or more alkaline earth metal carbonates). In other embodiments of the invention, the inorganic support material used in conjunction with a solid substrate, i.e., a subsupport or substructure composed of a more conventional support material, such as alumina (preferably, alpha-alumina). This latter type of support may employ the carbonate material coated on individual, relatively small particles of substructure or subsupport or on a larger unit such as a three-dimensional framework having a honeycomb-type of structure.

A granular form of the carbonate support material is preferred in the present invention, particularly when used as the exclusive or predominant component of the support. Commercially available carbonate materials suitable for use in the present invention may be obtained as powders which can be converted to the preferred granular form by conventional methods, including those described in Canadian Pat. No. 1,282,772. As described in greater detail below, the carbonate support may then be impregnated, or coated, with a solution containing a silver compound and a gold compound and thereafter reduced to provide a catalyst containing silver and gold in the elemental state.

Alternatively, as described below, the powdered carbonate support material may be combined with appropriate silver-containing and gold-containing solutions or a solution containing both silver and gold compounds, such as those used conventionally to impregnate solid supports, to form a slurry or paste. This material may then be spread on a suitable surface and dried and calcined at an appropriate temperature, such as about 500° C. This results in a carbonate support with silver and gold being supported thereon in their elemental state. The catalyst may then be impregnated with solutions of the potassium salt and/or the optional molybdenum promoter and thereafter dried. As an alternative, the potassium salt and/or molybdenum promoter may be dissolved in the same precious metal-containing impregnation solution used to form the coating paste or slurry with the carbonate material.

The carbonate support material, before or after incorporation of the silver, gold, potassium salt, and/or molybdenum promoter, can be formed into shaped composites suitable for use in propylene oxide manufacture. The composites may be formed by any suitable technique. For instance, it is possible to form the composites by compressing the support materials into a mold having a desired configuration. The size of the particles may be selected to be appropriate for the formation of the composite and are often in the range of about 0.001 to about 5 millimeters in major dimension.

When coated catalysts, i.e., those catalysts in which the carbonate material is coated on a substructure are employed, a slurry of the carbonate material, in either powder or granular form, may be mixed with the particle of support material and thereafter dried. As with the predominant or exclusive carbonate support materials described above, the coated catalysts may also be prepared by using a solution of (a) silver and gold compounds, (b) silver and gold compounds, potassium salt, and molybdenum promoter, (c) silver and gold compounds and potassium salt or (d) silver and gold compounds and molybdenum promoter to form the slurry, followed by suitable drying and, optionally, calcination.

The surface areas of the carbonate support materials generally range from 0.6 to about 14 $m^2/g$, preferably from about 1.5 to about 10 $m^2/g$. However, carbonate support materials having surface areas higher than 14 $m^2/g$ are also effective for the purposes of this invention. The surface is measured by the conventional B.E.T. method using nitrogen or krypton described by Brunauer, Emmett and Teller in *J. Am. Chem. Soc.* 60, 309–16 (1938).

The carrier materials used in the present invention may generally be described as porous or microporous and typically have water pore volumes of about 0.05 to 0.80 cc/g.

The supported catalysts are typically used as individual particles of irregular shape and size. This is true both for the predominate or exclusive carbonate supports as well as the carbonate-coated supports. However, in some instances the supports, particularly the carbonated-coated supports, may have a particular shape and size and this is especially true of the subsupports used with the carbonates. Typically the subsupports are formed into aggregates or "pills" of a size and configuration to be usable in tubular reactors. These pills may be formed by conventional extrusion and firing techniques. The pills generally range in size from about 2 mm to about 15 mm, preferably about 3 mm to about 12 mm, the size being chosen to be consistent with the type of reactor employed. In general, in fixed bed reactor applications, sizes ranging from about 3 mm to about 10 mm have been found to be most suitable in the typical tubular reactors used in commerce. The shapes of the carrier aggregates useful for purposes of the present invention can vary widely and can be any of the forms conventionally used in heterogeneous catalyst art.

It has been unexpectedly discovered that exceptionally high selectivity to the desired propylene oxide product is only obtainable by careful selection of composition of the supported catalyst. The catalyst must contain not only an alkaline earth metal carbonate support and silver but also a potassium promoter as well as gold. The support may be present either as predominately or exclusively the carbonate, designated herein as "carbonate-support". The corresponding catalysts which include such support are designated "carbonate-supported catalysts". When the carbonate is coated on or in the presence of a substrate or subsupport, the support is designated "carbonate-coated support" and when the support is used in a complete catalyst, the designation for the catalyst is a "carbonate-coated catalyst". As used herein, the term "coated" is not intended to imply that one substance necessarily forms a layer on or envelopes a second substance but merely refers to the procedure involved in the preparation of such material.

The carbonate- and carbonate-coated supports may be prepared as indicated above or obtained commercially. The carbonate-supported catalyst of the present invention may be prepared by any known method of introducing silver, gold and/or a potassium salt, such as potassium nitrate, in soluble form, and/or a molybdenum promoter, in soluble form, to a support. A preferred method of introducing silver and gold to the carbonate support is by an impregnation process in which a soluble salt or complex of silver and a soluble salt or complex of gold in amounts sufficient to deposit the desired weight of silver and gold upon the carrier, are dissolved in a suitable solvent or "complexing/solubilizing" agent. The solution may be used to impregnate the support or carrier by immersing the carrier in the precious metal-containing impregnating solution and forming a pasty mixture or slurry. The slurry is then dried and, optionally, calcined by placing the mixture in an oven or furnace at about 100° to about 120° C. for 0.5 to 6 hours and then heating the mixture at a temperature of from about 250° to about 600° C. for another 1 to 6 hours (preferably, under a reducing environment such as 5–10 volume % $H_2$ in $N_2$ or other inert gas). This procedure accomplishes drying of the carbonate/precious metal mixture, removes volatile components and reduces the silver and gold present to their elemental form.

The required potassium salt may be introduced to the catalyst as an impregnation solution in a separate impregnation step. Again, this may be done by any known manner of impregnating a porous material. Conveniently, this may be carried out by placing the catalyst material in a container, evacuating the container and thereafter introducing the salt solution. Alternatively, the support may be sprayed or sprinkled with the impregnating solution. The excess solution may then be allowed to drain off or the solvent may be removed by evaporation under reduced pressure at a suitable temperature. Incipient wetness impregnation techniques may also be used, if desired. The catalyst may then be dried at a moderate temperature (e.g., at 120° C.) in a oven for one-half to five hours. Such a procedure is known as "sequential" or "consecutive" method of preparation. The carbonate-supported catalyst may also be prepared by a "simultaneous" or "coincidental" method of preparation. With this method, the potassium salt is included in the solution or solutions containing the gold compound and/or silver compound used to impregnate the carbonate support.

The carbonate-coated catalysts are prepared by coating a suitable substructure or subsupport material, preferably alumina, and most preferably alpha alumina with a carbonate-containing slurry. This may contain only the carbonate, in which case the carbonate-coated support is further treated as indicated above to produce a precious metal or a precious metal and potassium salt supported on a carbonate-coated catalyst. Alternatively, a carbonate/precious metal compound slurry or a carbonate/precious metal compound/potassium salt slurry or a carbonate/precious metal compound/molybdenum promoter slurry or a carbonate/precious metal compound/potassium salt/molybdenum promoter slurry may be produced in a sequential or coincidental procedure. Thus, in a sequential procedure, particles or pills of a suitable subsupport material, such as alpha-alumina, are coated with a slurry of a carbonate material, a soluble salt or complex of gold and a soluble salt or complex of silver dissolved in a complexing/solubilizing agent. The particles or pills are thereafter drained and calcined in an oven at a temperature of about 250° to about 600° C. for about three minutes to about four hours, the duration of heating being inversely proportional to the temperature employed. The catalyst is then impregnated in the manner described above with a solution of potassium salt followed by (if so desired) a solution of molybdenum promoter, and then dried. The carbonate-coated supports may also be formed by a coincidental procedure in which a carbonate/precious metal compound/potassium salt/molybdenum promoter slurry is used to coat particles or pills of a suitable subsupport. After draining, the catalyst is dried at a temperature and for a duration indicated above for those carbonate-coated catalysts prepared by the sequential procedure.

The particular silver salt or compound used to form the precious metal-containing impregnating solution in a solvent or a complexing/solubilizing agent is not particularly critical and any silver salt or compound generally known to the art which is both soluble in and does not react with the solvent or complexing/solubilizing agent to form an unwanted product may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, generally the silver salts of higher fatty acids, and the like.

Although, generally speaking, the particular gold compound used to form the precious metal-containing impregnating solution is not critical, it has surprisingly been found that when gold chloride ($HAuCl_4$) is employed the resulting catalyst exhibits unsatisfactorily low propylene oxide selectivity particularly when gaseous promoters such as nitric acid and alkyl halides are not present in the feed stream. The result was unexpected in view of the fact that prior art olefin oxidation catalysts containing both silver and gold have nearly always used gold chloride to introduce gold into the catalyst. The gold compound selected for use should be both soluble in and non-reactive with the solvent or complexing/solubilizing agent. Gold hydroxide and gold carboxylates such as gold acetate are particularly preferred for use since such compounds tend to provide catalysts exhibiting superior propylene oxide selectivity.

A large number of solvents or complexing/solubilizing agents may be suitably used to form the precious metal-containing impregnating solution or solutions. Besides adequately dissolving the precious metal or converting it to a soluble form, a suitable solvent or complexing/solubilizing agent should be capable of being readily removed in subsequent steps, either by washing, volatilizing or oxidation procedure, or the like. The complexing/solubilizing agent, preferably, should also permit solution to provide about 5 to about 50 percent silver and about 1 to 10 percent gold in the finished catalyst, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the precious metal-containing solutions are water, alcohols, including glycols, such as ethylene glycol, amines (including alkanolamines and alkyldiamines) and carboxylic acids, such as lactic acid, as well as aqueous mixtures of such materials.

As indicated above, after impregnation the precious metal-impregnated carrier particles are treated to convert the precious metal salts or complexes to silver metal and gold metal and thereby effect disposition of silver and gold on the surface of the support. As used herein, the term "surface", as applied to the support, includes not only the external surface of the carrier but also the internal surfaces, that is, the surfaces defining the pores or internal portion of the support particles. This may be done by treating the impregnated particles with a reducing agent, such as hydrogen or hydrazide and/or by roasting the precious metals to their free metallic state. Certain solubilizing agents such as alkanolamines, alkyldiamines, and the like may also function as reducing agents.

A particularly preferred method of preparing supported catalysts suitable for use in the epoxidation process described herein is as follows. A solution comprising water, a gold compound and a silver compound is combined with the alkaline earth metal carbonate support. The resulting mixture is thereafter contacted with hydrogen under conditions effective to reduce the gold and silver compounds to their elemental state. Typical reduction conditions are: 200° C. to 300° C., 1000 to 3000 GHSV, 1 to 10% $H_2$ in an inert gas such as nitrogen, 1 to 18 hours. The potassium salt is thereafter introduced in the form of an aqueous solution onto the hydrogen-treated catalyst, preferably using incipient wetness impregnation methods. After drying and/or calcination, the desired supported catalyst in active form is obtained.

Although at least a catalytically effective amount of silver must be present in the finished catalyst (meaning an amount that provides a measurable conversion of propylene oxide), the silver concentration preferably is from about 2 percent to 70 percent, by weight, based on the total weight of the catalyst. More preferably, the silver concentration ranges from about 5 to 50 percent, by weight.

The amount of gold present in the finished catalyst should be, at a minimum, an amount effective to improve the epoxide selectivity of the catalyst as compared to its epoxide selectivity in the absence of gold. Preferably, the gold concentration ranges from about 1 to 10 weight percent based on the total weight of the catalyst.

It has been discovered that the presence of certain specific potassium promoters in the supported silver catalyst significantly enhances the efficiency of said catalyst as a propylene epoxidation catalyst. These promoters are derived from potassium salts wherein the anion is a nitrogen oxyanion (i.e., an anion or negative ion which contains both nitrogen and oxygen atoms) such as nitrate and nitrite or a carbon oxyanion (i.e., an anion or negative ion which contains both carbon and oxygen atoms) such as carbonate and bicarbonate or precursors thereof (i.e., an anion capable of undergoing displacement or other chemical reaction and forming a nitrogen or carbon oxyanion under epoxidation or catalyst preparation or pretreatment conditions). Potassium nitrate ($KNO_3$), potassium nitrite ($KNO_2$), and potassium carbonate ($K_2CO_3$) are the preferred potassium salts.

The efficiency-enhancing potassium salt may be introduced to the catalyst in any known manner. Thus, impregnation and deposition of silver, gold and a potassium salt may be effected coincidentally or sequentially, as described above. The preferred method is a sequential impregnation of the support wherein initial introduction of a precious metal-containing solution is followed by drying of the precious metal-containing support and heating and/or chemical reduction of the gold and silver. This support is then impregnated with a solution of the potassium salt.

In order to perform coincidental impregnation, the potassium salt must be soluble in the same solvent or complexing/ solubilizing liquid used with the silver impregnating solution, the gold impregnating solution or the silver/gold impregnating solution. With the preferred sequential procedure in which the silver and gold are added first simultaneously, any solvent capable of dissolving the silver and gold compounds which will neither react with the precious metals nor leach them from the support is suitable. Aqueous solutions are generally preferred, but organic liquids, such as alcohols, may also be employed. Suitable procedures for effecting introduction of the potassium salt to the solid support are well known in the art.

The required potassium salt is added in an amount sufficient to provide an improvement in one or more of the catalytic properties (e.g., selectivity, activity, conversion, stability, yield) of the supported catalyst as compared to a catalyst not containing the potassium salt (herein referred to as "promoting amount"). The precise amount will vary depending upon such variables as the identity and concentration of gaseous components in the feed stream, the amounts of silver and gold contained in the catalyst, the surface area of the support, the process conditions, e.g., space velocity and temperature, and the morphology of the support. Generally, however, a suitable concentration range of the added potassium salt, calculated as cation, is about 0.15 to about 5 percent, preferably about 0.5 to about 3 percent, by weight, based on the total weight of the catalyst. Most preferably, the salt is added in an amount of about 1.0 to about 2.5 weight percent K.

The addition of a promoting amount of molybdenum (i.e., an amount that works effectively to provide an improvement in one or more catalytic properties of a catalyst as compared to a catalyst not containing molybdenum) to a potassium salt-containing supported silver-gold catalyst may help to further improve the performance of such catalyst. In particular, it has been discovered that selectivity to propylene oxide can be increased and the rate of catalyst deactivation can be decreased by incorporating molybdenum into the catalyst. Transition metal compounds other than Mo compounds may also be similarly introduced into the catalyst. The exact form of the promoter under epoxidation operating conditions is not known. The molybdenum promoter, it is believed, is not present on the catalyst in the elemental form since the promoter is applied to the catalyst in the form of ions, salts, compounds, and/or complexes and the reducing conditions generally used to reduce the silver to metallic silver and the gold to metallic gold are not usually sufficient to reduce the molybdenum to the elemental form.

It is thought that the molybdenum promoter deposited on the support or present on the catalyst is in the compound form, most probably in the form of an oxygen-containing or oxidic compound. In a presently preferred embodiment, the promoter is applied to the catalyst in the oxyanionic form, i.e., in the form of an anion, or negative ion which contains oxygen. Examples of anions of molybdenum that can be suitably applied include molybdate, dimolybdate, paramolybdate, other iso- and hetero-polymolybdates, phosphomolybdate, and the like. The anions can be prepared by the reactive dissolution of various non-anionic materials such as the oxides such as $MoO_3$ etc., as well as other materials such as carbonates, sulfates, halides, oxyhalides, hydroxyhalides, hydroxides, sulfides, etc., of molybdenum. Alkali metal and ammonium salts of molybdenum oxyanions (e.g., potassium molybdate, ammonium molybdate) may be utilized.

In this embodiment of the invention, the carrier is impregnated with molybdenum promoter ions, salt(s), compound(s) and/or complex(es). This may be done at the same time that the other components of the catalyst are added or before and/or later. Preferably the molybdenum promoter, gold and silver are incorporated into the catalyst prior to the addition of the potassium salt.

The preferred amount of optional molybdenum promoter compound present on or deposited on the support ranges from about 0.05 to 2.5 weight percent Mo (measured as the element irrespective of the form in which the promoter is present) based on the total weight of the supported catalyst. The degree of benefit obtained within the above-defined limits will vary depending upon particular properties and characteristics, such as, for example, reaction conditions, catalyst preparative techniques, surface area and pore structure and surface chemical properties of the support utilized, precious metal content of the catalyst, and potassium content of the catalyst.

The presence of the indicated and claimed amounts of gold, potassium promoter, and molybdenum promoter in this specification and claims does not preclude the use of other activators, promoters, enhancers, stabilizers, improvers, and the like. However, the present invention has unexpectedly been found to be capable of operating at relatively high efficiency even in the absence of such additional components.

The molybdenum promoter compounds, salts and/or complexes optionally used in the preparation of the instant catalysts are molybdenum compounds, salts and/or complexes that can be solubilized in an appropriate solvent. Preferably, the solvent is a water-containing solvent. More preferably the solvent is the same solvent used to deposit the silver, gold and potassium salt. Preferred promoter compounds are the oxyanionic compounds of molybdenum preferably the ammonium and alkali metal oxyanionates, such as potassium molybdate, cesium molybdate, rubidium molybdate, ammonium molybdate, lithium molybdate, sodium molybdate and the like.

Propylene and an oxygen-containing gas (i.e., a gas comprising molecular oxygen) are brought together in a reactor in the presence of the previously described catalyst under conditions effective to accomplish at least partial epoxidation of the propylene. Typical epoxidation conditions include temperatures within the reaction zone of the reactor on the order of about 180° to 350° C. (more preferably, 200° to 300° C.) and pressures from about 1 to about 30 atmospheres. Inlet pressures may be as low as 14 to 75 psig. To favor high selectivity to epoxide, it is desirable that the feed stream contain carbon dioxide. An organic halide and/or a gaseous nitrogen oxide species (described in more detail hereafter) may also optionally be supplied to the reaction zone within the reactor by introducing said species to the feed stream, containing propylene (fresh and/or recycled) and molecular oxygen. However, the presence of such species is not necessary in order to attain relatively high catalyst activity and selectivity. In fact under certain conditions, the addition of an organic halide to the feedstream actually is detrimental to catalyst performance, since it tends to accelerate the rate of catalyst deactivation. This result was unexpected in view of the general belief in the art that organic halides improve the efficiency of supported silver oxidation catalyst.

Examples of nitrogen oxide species suitable for optional introduction in the feed stream include at least one of NO, $NO_2$, $N_2O_4$, $N_2O_3$ or any gaseous substance capable of forming one of the aforementioned gases, particularly NO and $NO_2$, under epoxidation conditions, and mixtures of one of the foregoing, particularly, $NO_2$, with one or more of CO, PH$_3$, SO$_3$ and SO$_2$. NO$_2$ is the most preferred nitrogen oxide species. Inclusion of such nitrogen oxide species in the feed stream is not necessary, however.

The amount of gaseous nitrogen oxide species present (if any) is not critical. The optimum amount is determined, in part, by the particular potassium salt used and the concentration thereof, and by other factors noted above which influence the optimum amount of potassium salt. Typically, a suitable concentration of the nitrogen oxide species for epoxidation of propylene, is about 0.1 to about 2,000 ppm, by volume, when N$_2$ is used as a ballast. When NO$_2$ is used in epoxidation of propylene, the preferred concentration is about 5 to about 2,000 ppm, more preferably about 20 to 500 ppm, by volume, with an N$_2$ ballast. However, as explained previously, the nitrogen oxide species concentration may be essentially zero.

The "oxygen" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. The oxygen is typically introduced to the reactor either as air, commercially pure oxygen or other substance which under epoxidation conditions both exists in a gaseous state and forms molecular oxygen.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feed stream having the particular composition previously described thus may be formed prior to or at the time the individual components thereof enter the reaction zone. The use of term "feedstream" herein thus is not meant to limit the present process to the embodiment where all of the gaseous components are combined prior to introduction of said components into the reaction zone. The reactors in which the process and catalyst of the present invention are employed may be of any type known to the art. A brief description of several of the reactor parameters which may be used in the present invention is presented below.

Carbon dioxide is desirable to include as a component of the feedstream in the epoxidation process of this invention. The presence of carbon dioxide, within certain limits, has been found to provide surprising improvements in propylene oxide selectivity. Desirable enhancements of selectivity are generally observed using 1 to 60 volume % CO$_2$ in the feedstream, with 5 to 25 volume % CO$_2$ being preferred.

The components of the feedstream are most suitably present in the amounts shown on the following table

| Component | Volume in % (or ppm) for Propylene Oxidation |
|---|---|
| propylene | about 2 to about 50% |
| oxygen | about 2 to about 10% |
| organic halide | preferably, 0 |
| nitrogen oxide species | 0 to about 2,000 ppm |
| hydrocarbon other than propylene | 0 to about 5% |
| carbon dioxide | 0 to 60%, more preferably 5 to 25% |
| nitrogen or other ballast gas | remainder |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxidation reactors. These generally include wall-cooled as well as adiabatic or non-wall-cooled reactors. Tube lengths may typically range from about 5 to about 60 feet but will frequently be in the range from about 15 to about 45 feet. The tubes may have internal diameters from about 0.5 to about 2.5 inches and are expected to be typically from about 0.8 inches to about 1.5 inches. A plurality of tubes packed with catalyst arranged in parallel within a suitable shell may be employed. GHSV values generally range from about 500 to about 10,000 (more typically, from about 800 to about 3,000). Pressures of from about 1 to about 30 atmospheres, more commonly about 1.1 to about 5 atmospheres, may be utilized. The contact time should be sufficient to convert 0.5 to 70%, preferably 5 to 30%, of the propylene as it passes through the reactor.

EXAMPLES

Example 1

This example illustrates the preparation of a supported catalyst in accordance with the invention. Silver nitrate (5.61 g) was dissolved in 20 ml distilled water. To this well-mixed solution was added gold hydroxide (0.91 g) followed by calcium carbonate (10 g). The resulting mixture was dried at 110° C. for 4 hours and then hydrogen treated for 4 hours at 250° C. and 3000 GHSV using a feed of 5% hydrogen in nitrogen. By incipient wetness impregnation, an aqueous solution of potassium nitrate (0.24 g) dissolved in 10 ml of distilled water was added to the hydrogen treated product (9.36 g). The resulting product was then dried at 110° C. for 5 hours to yield a calcium carbonate-supported catalyst containing 25 weight % Ag, 4.6 weight % Au, and 1 weight % K.

Example 2

A calcium carbonate-supported catalyst (2 cc; 2.39 g; 14–30 mesh) containing 25 weight % Ag, 4.6 weight % Au, 1 weight % K (as K$_2$CO$_3$) was charged to a micro reactor. At conditions of 250° C., 30 psig and 1200 GHSV, a feedstream containing 10 volume % propylene, 5 volume % O$_2$, and 200 ppm NO$_2$, with the balance being nitrogen, was passed over the catalyst. After 24 hours on line, 6% propylene conversion and 44% selectivity to propylene oxide were obtained. The remainder of the product was carbon dioxide. The rate of catalyst deactivation under the test conditions was relatively low (approximately 6 ppm propylene oxide per hour).

Examples 3–4

These examples demonstrate that relatively high selectivity to propylene oxide is obtainable using the process of this invention even in the absence of gaseous promoters (NO$_x$ and/or organic halide). A calcium carbonate-supported catalyst (2 cc; 14–30 mesh) containing 25 weight % Ag, 4.6 weight % Au (derived from Au(OH)$_3$), and 2 weight % K (derived from KNO$_3$) was charged to a 0.5 inch diameter, tubular, fixed bed reactor. At conditions of 250° C., 30 psig, and 1200 GHSV using a feedstream comprised of 10 volume % propylene, 5 volume % O$_2$, and no gaseous promoters, with the balance being N$_2$, results of 2% propylene conversion and 40% selectivity to propylene oxide were obtained. By way of comparison, a fresh charge of the same catalyst under the same conditions, except with 200 ppm NO and 50 ppm ethyl chloride added to the feedstream, gave identical results.

Example 5

This example illustrates the embodiment of the invention wherein a molybdenum promoter is present in the mixed precious metal supported catalyst. A calcium carbonate-supported catalyst containing 25 weight % Ag, 4.6 weight % Au, 0.5 weight % Mo (from ammonium molybdate) and 1 weight % K (from $KNO_3$) was prepared in accordance with the procedure of Example 1. A portion of the catalyst (2 cc; 14–30 mesh) was charged to a microreactor. At conditions of 250° C., 30 psig and 1200 GHSV, a feedstream containing 10 volume % propylene, 5 volume % $O_2$ with the balance being nitrogen, was passed over the catalyst. After 10 hours on line, 2% propylene conversion and 50% selectivity to propylene oxide were observed. The remainder of the product was carbon dioxide.

We claim:

1. A process for producing propylene oxide wherein a feedstream comprising oxygen and propylene is contacted in the vapor phase at a temperature of 180° C. to 350° C. with a supported catalyst comprising
   (a) a support comprising an alkaline earth metal carbonate;
   (b) a catalytically effective amount of silver;
   (c) an amount of gold effective to improve selectivity to propylene oxide, wherein said gold is derived from a gold compound selected from the group consisting of gold hydroxide, gold carboxylates and mixtures thereof; and
   (d) a promoting amount of a potassium promoter derived from a potassium salt comprising potassium cation and an anion selected from carbon oxyanions, nitrogen oxyanions and precursors thereof.

2. The process of claim 1 wherein the alkaline earth metal carbonate is calcium carbonate.

3. The process of claim 1 wherein the potassium salt is selected from the group consisting of potassium carbonate, potassium bicarbonate, potassium nitrate, potassium nitrite and mixtures thereof.

4. The process of claim 1 wherein the supported silver catalyst is comprised of 5 to 50 weight percent silver based on the total weight of the supported silver catalyst.

5. The process of claim 1 wherein the potassium promoter is present in an amount of from 0.5 to 3 percent by weight, calculated as potassium cation, based on the total weight of the supported silver catalyst.

6. The process of claim 1 wherein the amount of gold present is from 1 to 10 weight percent based on the total weight of the supported silver catalyst.

7. The process of claim 1 wherein the feedstream is characterized by the absence of an organic halide.

8. A process for producing propylene oxide wherein a feedstream comprising oxygen and propylene is contacted in the vapor phase at a temperature of 200° C. to 300° C. with a supported silver catalyst comprising
   (a) a support comprising calcium carbonate;
   (b) from 5 to 50 percent, based on the total weight of supported catalyst, of silver;
   (c) from 1 to 10 weight percent, based on the total weight of supported catalyst, of gold, wherein said gold is derived from a gold compound selected from the group consisting of gold hydroxide, gold carboxylates, and mixtures thereof; and
   (d) from 0.5 to 3 percent by weight, calculated as potassium cation based on the total weight of supported silver catalyst, of a potassium promoter derived from a potassium salt selected from the group consisting of potassium carbonate, potassium bicarbonate, potassium nitrate, potassium nitrite and mixtures thereof.

9. The process of claim 8 wherein the feedstream is characterized by the absence of an organic halide.

10. The process of claim 8 wherein the supported silver catalyst additionally comprises a promoting amount of a molybdenum promoter.

11. A process for producing propylene oxide wherein a feedstream comprising oxygen and propylene and characterized by the absence of an organic halide is contacted in the vapor phase at a temperature of 180° C. to 350° C. with a supported catalyst comprising
   (a) a support comprising an alkaline earth metal carbonate;
   (b) a catalytically effective amount of silver;
   (c) an amount of gold effective to improve selectivity to propylene oxide; and
   (d) a promoting amount of potassium promoter derived from a potassium salt comprising potassium cation and an anion selected from carbon oxyanions, nitrogen oxyanions and precursors thereof.

12. The process of claim 11 wherein the alkaline earth metal carbonate is calcium carbonate.

13. The process of claim 11 wherein the potassium salt is selected from the group consisting of potassium carbonate, potassium bicarbonate, potassium nitrate, potassium nitrite and mixtures thereof.

14. The process of claim 11 wherein the supported silver catalyst is comprised of 5 to 50 weight percent silver based on the total weight of the supported silver catalyst.

15. The process of claim 11 wherein the potassium promoter is present in an amount of from 0.5 to 3 percent by weight, calculated as potassium cation, based on the total weight of the supported silver catalyst.

16. The process of claim 11 wherein the gold is derived from a gold compound selected from the group consisting of gold hydroxide, gold carboxylates and mixtures thereof.

17. The process of claim 11 wherein the amount of gold present is from 1 to 10 weight percent based on the total weight of the supported silver catalyst.

18. A process for producing propylene oxide wherein a feedstream comprising oxygen and propylene and characterized by the absence of an organic halide is contacted in the vapor phase at a temperature of 200° C. to 300° C. with a supported silver catalyst comprising
   (a) a support comprising calcium carbonate;
   (b) from 5 to 50 percent, based on the total weight of supported catalyst, of silver;
   (c) from 1 to 10 weight percent, based on the total weight of supported catalyst, of gold; and
   (d) from 0.5 to 3 percent by weight, calculated as potassium cation based on the total weight of supported silver catalyst, of a potassium promoter derived from a potassium salt selected from the group consisting of potassium carbonate, potassium bicarbonate, potassium nitrate, potassium nitrite and mixtures thereof.

19. The process of claim 18 wherein the gold is derived from a gold compound selected from the group consisting of gold hydroxide, gold carboxylates, and mixtures thereof.

20. The process of claim 18, wherein the supported silver catalyst additionally comprises a promoting amount of a molybdenum promoter.

* * * * *